(12) United States Patent
Persaud

(10) Patent No.: US 11,168,282 B2
(45) Date of Patent: Nov. 9, 2021

(54) FRAGRANCE COMPOSITIONS COMPRISING ESSENTIAL OILS AND PRODUCTS COMPRISING SAME FOR REDUCING FATIGUE AND IMPROVING BRAIN FUNCTION

(71) Applicant: THIS WORKS PRODUCTS LIMITED, London (GB)

(72) Inventor: Anna Persaud, London (GB)

(73) Assignee: THIS WORKS PRODUCTS LIMITED, London (GB)

( * ) Notice: Subject to any disclaimer, the term of this patent is extended or adjusted under 35 U.S.C. 154(b) by 0 days.

(21) Appl. No.: 16/593,548

(22) Filed: Oct. 4, 2019

(65) Prior Publication Data

US 2020/0109346 A1    Apr. 9, 2020

(30) Foreign Application Priority Data

Oct. 5, 2018 (GB) ...................... 1816277

(51) Int. Cl.
| | | |
|---|---|---|
| *C11B 9/00* | (2006.01) | |
| *A61K 8/9789* | (2017.01) | |
| *A61K 36/53* | (2006.01) | |
| *A61K 36/534* | (2006.01) | |
| *A61Q 19/00* | (2006.01) | |
| *C11C 5/00* | (2006.01) | |

(52) U.S. Cl.
CPC .............. *C11B 9/00* (2013.01); *A61K 8/9789* (2017.08); *A61K 36/53* (2013.01); *A61K 36/534* (2013.01); *A61Q 19/007* (2013.01); *C11C 5/002* (2013.01)

(58) Field of Classification Search
None
See application file for complete search history.

(56) References Cited

U.S. PATENT DOCUMENTS

| | | | |
|---|---|---|---|
| 2002/0034556 A1 | 3/2002 | Khazan | |
| 2006/0083763 A1* | 4/2006 | Neale ..................... | A01N 65/06 424/405 |
| 2013/0303432 A1 | 11/2013 | Hoelscher et al. | |
| 2015/0150922 A1* | 6/2015 | Hefti ..................... | A61K 36/61 424/733 |

FOREIGN PATENT DOCUMENTS

| | | |
|---|---|---|
| EP | 2298275 A1 | 3/2011 |
| KR | 20060029948 A | 4/2006 |
| WO | 02098439 A1 | 12/2002 |

OTHER PUBLICATIONS

Database GNPD, Mintel; Jan. 31, 2014, anonymous: "Day Cream", XP055640149, retrieved from www.gnpd.com, Database accession No. 2225978.
International Search Report and Written Opinion issed in co-pending International application No. PCT/GB2019/052822 dated Dec. 4, 2019.
English translation of KR20060029948.

* cited by examiner

*Primary Examiner* — Susan Hoffman
(74) *Attorney, Agent, or Firm* — BCF LLP

(57) ABSTRACT

The present technology generally relates to fragrance compositions comprising essential oils and products comprising the same. The present technology also relates to methods of using the fragrance compositions to reduce fatigue and improve executive brain function.

17 Claims, 5 Drawing Sheets

FRAGRANCE COMPOSITIONS COMPRISING ESSENTIAL OILS AND PRODUCTS COMPRISING SAME FOR REDUCING FATIGUE AND IMPROVING BRAIN FUNCTION

CROSS-REFERENCE TO RELATED APPLICATION

This application claims the benefit of and priority to UK patent application No. 1816277.6, filed on Oct. 5, 2018; the content of all of which is herein incorporated in entirety by reference.

FIELD OF TECHNOLOGY

The present technology generally relates to fragrance compositions comprising essential oils and products comprising the same. The present technology also relates to methods of using the fragrance compositions to reduce fatigue and improve executive brain function.

BACKGROUND OF TECHNOLOGY

For a long time, fragranced substances (odors, aromas, scents, perfumes) have been used for mental, psychological, physiological, and even spiritual purposes, to address disorders and aide well-being. Despite this, and the finding that it is the most basic and evocative of our senses (Herz, 2004), olfaction has declined in importance as a sensory modality. Its significance is, however, gradually increasing in both the cosmetic and medicinal industries.

Studies have reported that olfactory stimulation through odor inhalation, application on the skin, massages, or bathes may have psycho-physiological impacts (Haehner, Antje et al 2017; Bower 2005; Liljenkvist et al, 2010). Interest in this sense is also driven by the search for non-pharmacological approaches to address health issues associated with the stress of the modern life style, such as in disorders of sleep and alertness, and a lack of relaxation.

Olfaction is complex and understanding the mechanism of odor perception is important for achieving an optimal impact of odors on the brain. There is a direct connection from olfactory neurons to the limbic and memory centres of the brain (Gottfried, 2006). The olfactory system may be viewed as an extension of this limbic system, which governs emotions and behaviours (e.g. aggression, fear, mating). Further, it is the only sensory system that connects directly with behavioural centres without the requirement of processing information in other centres, such as the thalamus. Hence a direct behavioural response can be elicited by a particular odorant, which may also be linked to the memory of that odorant.

SUMMARY OF TECHNOLOGY

The present inventors have identified that particular blends of essential oils stimulate activity in regions of the brain closely linked to alertness and the ability to focus. It follows therefore, that these blends may be particularly useful in enhancing performance after a period of sleep, particularly in subjects that may be sleep-deprived.

In a first aspect, the present technology provides a fragrance composition comprising:
(a) *Lavandula hybrida* Oil;
(b) *Rosmarinus offinalis* Leaf Oil; and
(c) *Mentha piperita* Oil.

In certain embodiments, the fragrance compositions consist essentially of or consist of essential oils. In certain embodiments, the fragrance composition consists essentially of or consists of (a) *Lavandula hybrida* Oil; (b) *Rosmarinus offinalis* Leaf Oil and (c) *Mentha piperita* Oil.

In further aspects, the present technology provides products comprising the fragrance compositions according to the first aspect of the present technology. Such products include but are not limited to cosmetic products (for example a cream, a lotion, a spray composition, an infused wipe, a face mask, drops, body oils), candles, spray devices.

In further aspects, the present technology provides methods of using the fragrance compositions according to the first aspect of the present technology. For example, the present technology relates to methods of reducing fatigue in a subject and/or methods of improving executive brain function in a subject by administering fragrance compositions in accordance with the present technology.

The present technology further relates to uses of fragrance compositions in accordance with the first aspect of the present technology for reducing fatigue and/or improving executive brain function in a subject.

Other aspects and features of the present disclosure will become apparent to those ordinarily skilled in the art upon review of the following description of specific embodiments.

DETAILED DESCRIPTION

Figure 1:
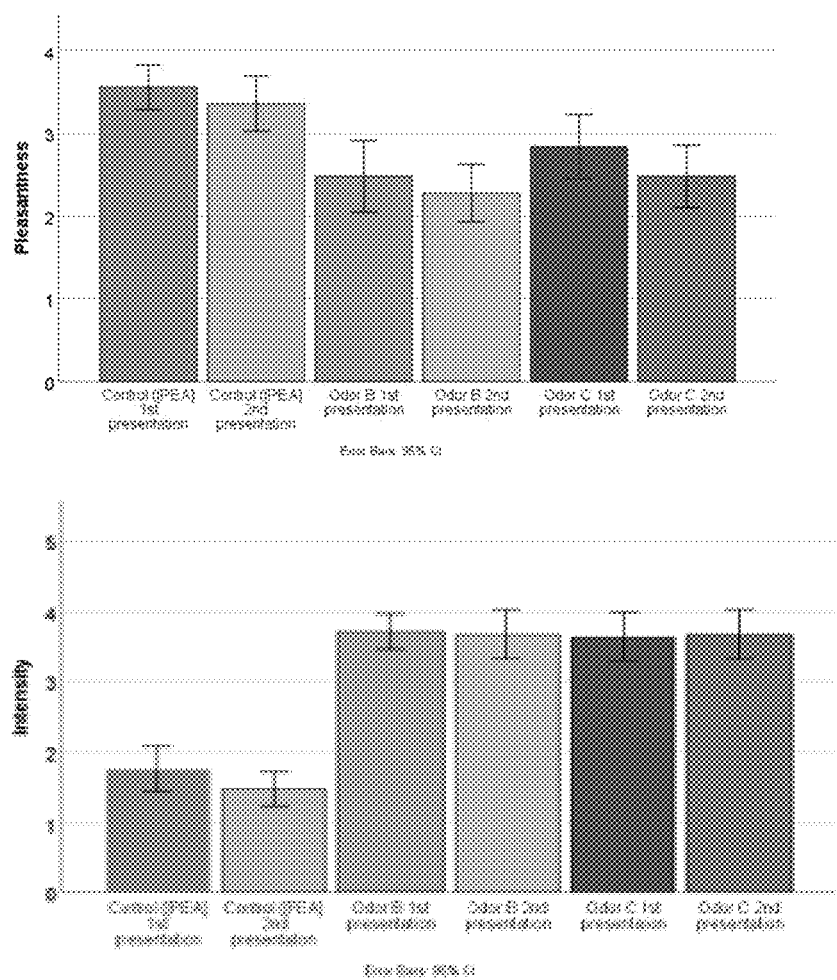
FIG. 1 Pleasantness and intensity ratings measured for odors B and C relative to a control fragrance. The error bars indicate the 95% confidence interval.

In a first aspect, the present technology provides fragrance compositions comprising blends of essential oils. The fragrance compositions of the present technology may also be referred to herein as "fragrances", "odors", "odours", "oil-blends". The fragrance compositions are intended for and are suitable for inhalation by human subjects. As described elsewhere herein, the fragrance compositions of the present technology find utility in improving performance typically after a period of sleep.

The fragrance compositions of the present technology comprise the following essential oil ingredients: (a) *Lavandula hybrida* Oil; (b) *Rosmarinus offinalis* Leaf Oil; and (c) *Mentha piperita* Oil. The common names for these three ingredients are Lavandin, Rosemary and Peppermint. Thus, the fragrance compositions of the present technology may alternatively be defined as comprising the essential oils (a) Lavandin; (b) Rosemary; and (c) Peppermint. These three oils may be combined so as form a composition of the present technology using any suitable technique known to those skilled in the art.

The relative amounts of ingredients (a), (b) and (c) may vary in the fragrance compositions of the present technology. In certain embodiments, the ratio of (a) *Lavandula hybrida* Oil to (b) *Rosmarinus offinalis* Leaf Oil is from about 1.5:1 to about 2.5:1. In certain embodiments, the ratio of (a) *Lavandula hybrida* Oil to (b) *Rosmarinus offinalis* Leaf Oil is about 2:1. Alternatively or in addition, the ratio of (b) *Rosmarinus offinalis* Leaf Oil to (c) *Mentha piperita* Oil is from about 1:1 to about 1.5:1. In certain embodiments, the ratio of (b) *Rosmarinus offinalis* Leaf Oil to (c) *Mentha piperita* Oil is about 1.3:1. In certain embodiments, the ratio of (a) *Lavandula hybrida* Oil to (b) *Rosmarinus offinalis* Leaf Oil to (c) *Mentha piperita* Oil is about 2.7:1.3:1.

The fragrance compositions of the present technology may comprise additional ingredients. For example, the compositions may comprise one or more additional essential oils selected from the group consisting of *Eucalyptus staigeriana* Leaf Oil, *Litsea cubeba*, Citrus Limon (Lemon) Peel Oil, *Eucalyptus smithii* Leaf Oil, *Ocimum basilicum* (Basil) Oil.

In certain embodiments, the fragrance compositions consist essentially of or consist of essential oils.

In certain embodiments, the fragrance compositions consist essentially of (a) *Lavandula hybrida* Oil; (b) *Rosmarinus offinalis* Leaf Oil; and (c) *Mentha piperita* Oil. In a preferred embodiment, the fragrance composition consists of (a) *Lavandula hybrida* Oil; (b) *Rosmarinus offinalis* Leaf Oil; and (c) *Mentha piperita* Oil. For embodiments wherein the fragrance composition consists essentially of or consists of (a) *Lavandula hybrida* Oil; (b) *Rosmarinus offinalis* Leaf Oil; and (c) *Mentha piperita* Oil, the compositions may include: (a) 50-58% *Lavandula hybrida* Oil; (b) 22-30% *Rosmarinus offinalus* Leaf Oil; and (c) 16-24% *Mentha piperita* Oil. For embodiments wherein the fragrance composition consists essentially of or consists of (a) *Lavandula hybrida* Oil; (b) *Rosmarinus offinalis* Leaf Oil; and (c) *Mentha piperita* Oil, the compositions may include: (a) 52-56% *Lavandula hybrida* Oil; (b) 24-28% *Rosmarinus offinalus* Leaf Oil; and (c) 18-22% *Mentha piperita* Oil. In a preferred embodiment, the fragrance composition consists of (a) about 54% *Lavandula hybrida* Oil; (b) about 26% *Rosmarinus offinalus* Leaf Oil; and (c) about 20% *Mentha piperita* Oil.

The present technology provides, in further aspects, methods and uses of the fragrance compositions described herein. As reported elsewhere herein, fragrance compositions of the present technology promote activation of brain regions associated with alertness and focus. As such, the fragrance compositions described herein can be used to improve the feeling of wellbeing or wellness and also performance in subjects, for example after a period of sleep.

In one aspect, the present technology provides methods of reducing fatigue in a subject, typically a human subject, by administering to the subject a fragrance composition in accordance with the first aspect of the present technology. The subject administered the fragrance may be a healthy individual, for example an individual without a pre-existing sleep disorder. The subject administered the fragrance composition may be sleep-deprived, for example may have slept for less than 7 hours, less than 6 hours, less than 5 hours, less than 4 hours in the 24 hour period preceding the administration of the composition. Alternatively or in addition, the subject administered the fragrance may be otherwise fatigued due to an underlying illness or condition, including but not limited to a sleep disorder. Thus, the present technology provides a fragrance composition in accordance with the first aspect of the present technology for use in reducing fatigue in a subject in need thereof.

In a further aspect, the present technology provides methods of improving executive brain function in a subject, typically a human subject, by administering to the subject a fragrance composition in accordance with the first aspect of the present technology. As described elsewhere herein, executive brain function is typically regulated by the dorsal lateral prefrontal cortex (DL PFC) and the fragrance compositions of the present technology are particularly effective for the activation of this brain region. It follows therefore, that the fragrance compositions in accordance with the present technology may be used to improve executive brain function. Different tests exist to measure executive brain function or "executive function" and methods in accordance with the present technology may be used to improve executive brain function as measured using any of the standard tests. For example, the Stroop test is a neuropsychological test used to evaluate executive function. The Behaviour Rating Inventory of Executive Function is another means by which to assess executive function, particularly in children and adolescents.

The subject administered the composition may be a healthy individual i.e. an individual without underlying health problems or problems with sleep. Alternatively, the subject may be an individual in need of improvements in executive brain function, for example an individual who is sleep deprived, for example a subject who has slept for less than 7 hours, less than 6 hours, less than 5 hours, less than 4 hours in the 24 hour period preceding the administration of the composition. The subject administered the composition of the present technology may a subject having a condition, disease or disorder that compromises executive brain function. Thus, the present technology provides a fragrance composition in accordance with the first aspect of the present technology for use in improving executive brain function in a subject in need thereof.

Also within the scope of the present technology are methods for improving any one or more of the following: cognition, attention, decision-making, memory, learning, perception, planning, and/or problem-solving in subjects in need thereof. Also within the scope of the present technology are methods for improving wellness, alertness, focus and/or positivity in subjects. All such methods comprise administering to the subject a fragrance composition in accordance with the present technology.

In accordance with the methods of the present technology, the fragrance composition may be administered to the subject directly following a period of sleep. For example, the composition may be administered to a subject within 15 minutes, within 30 minutes, within 1 hour, within 2 hours of waking from a period of sleep.

In accordance with the methods of the present technology, the fragrance compositions will preferably be administered to subjects via inhalation. Other modes of administration suitable for the delivery of essential oil blends may alternatively be used. Furthermore, as described herein below, the fragrance compositions may be incorporated into cosmetic products wherein the route of administration may be affected by the product intended for the end-user.

The present technology further provides uses of fragrance compositions in accordance with the first aspect of the present technology for reducing fatigue and/or improving executive brain function in subjects, typically human subjects.

In further aspects, the present technology provides products comprising the fragrance compositions according to the first aspect of the present technology. In one aspect, the present technology provides cosmetic products comprising a fragrance composition in accordance with any embodiments of the first aspect of the present technology. Cosmetic products that may comprise fragrance compositions described herein include but are not limited to creams, lotions, spray compositions, infused wipes, face masks, drops or droplets, body oils.

In certain embodiments, the fragrance compositions may be incorporated in skincare products, for example skincare products intended for topical administration. Such products include but are not limited to creams, lotions and body oils. For embodiments wherein the fragrance compositions are incorporated into products such as creams and lotions, the fragrance composition may be present in an amount from about 0.1 to about 5 wt %.

In certain embodiments, the fragrance compositions may be incorporated into cosmetic products that are formulated as sprays or droplets, for example perfumes and such like. In certain embodiments, the fragrance composition is incorporated into a spray composition.

For embodiments wherein the fragrance compositions are incorporated into cosmetic products, the cosmetic products may comprise additional ingredients, particularly standard ingredients used to formulate creams, lotions, perfumes, body oils suitable or intended for application to human skin. In certain embodiments, the products comprise vitamin C.

Further provided herein are products allowing for effective delivery of the fragrance composition to a subject. For example, the fragrance compositions in accordance with the present technology may be incorporated into candles such that the fragrance is released when the candle is burning. Products suitable for delivery of the fragrance compositions further include products capable of delivering the compositions in the form of a spray or droplets. Thus, provided herein is a spray device comprising a spray nozzle in fluid communication with a reservoir, the reservoir containing a fragrance composition according to any of the embodiments described herein and a volatile solvent.

The present technology will now be further understood with reference to the following non-limiting examples.

EXAMPLES

Example 1 Pilot Testing of Fragrances 1.1 Study Design:

10 normosmic participants were tested (4 men, 6 women, aged 20-36) who had slept between 5 and 8 hours the previous night. Three different odors "A" (Active Citrus), "B" (Active Mint Herb) and "C" (Active mint Eucalyptus) and a control odor (PEA-Phenylethylalcohol) were presented to the subjects that had agreed to participate in this small pilot study. The composition of odors A, B and C is shown in the Tables 1, 2 and 3, below.

TABLE 1

Odor A - Active *Citrus* INCI

| Common Name | INCI Name | % |
|---|---|---|
| Eucalyptus Staigeriana | *Eucalyptus Staigeriana* Leaf Oil | 30 |
| Litsea | *Litsea Cubeba* | 20 |
| Lemon | *Citrus Limon* (Lemon) Peel Oil | 50 |

TABLE 2

Odor B - Active Mint Herb

| Common Name | INCI Name | % |
|---|---|---|
| Peppermint | *Mentha Piperita* (Peppermint) Oil | 20 |
| Rosemary | *Rosmarinus Offinalus* (Rosemary) Leaf Oil | 26 |
| Lavandin | *Lavandula* Hybrida Oil | 54 |

TABLE 3

Odor C - Active Mint *Eucalyptus* INCI

| Common Name | INCI Name | % |
|---|---|---|
| Eucalyptus Smithii | *Eucalyptus Smithii* Leaf Oil | 25 |
| Lemon | *Citrus Limon* (Lemon) Peel Oil | 25 |
| Peppermint | *Mentha Piperita* | 25 |
| Basil | *Ocimum Basilicum* (Basil) Oil | 25 |

Each odor was presented three times, which results in three randomised blocks, and in every block each odor was presented once. The four odors were presented to the participants by a research assistant and participants smelled the odor with closed eyes and then rated the presented odor on three visual analogue rating scales (VAS) on the aspects of pleasantness, intensity and calmness (0-1 from very unpleasant to very pleasant, very mild to very intense, and very energising to very calming). The procedure has been adapted from Clepse et al (2014) were recommended the use of VAS for odor ratings based on previous research on validity and reliability. For results presentation, the values are reported as percentages.

Prior to the odor rating, participants assessed the hours of sleep they had the previous night and filled out the Positive and Negative Affect Schedule (PANAS) and the Karolinska Sleepiness Scale (KSS). The PANAS is a self-report questionnaire that consists of two 10-item scales to measure both positive and negative effect. Each item is rated on a Likert scale of one (not at all) to 5 (very much). Reliability is a high for both the PA scale (Cronbach=0.89) and the NA scale (Cronbach=0.85) and construct validity was found to be adequate.

As a second covariate, the participant's sleepiness has been assessed through the KSS. The KSS is a 9-Likert scale often used when conducting studies involving self-reported, subjective assessment of an individual's level of drowsiness at the time. It has been shown that there is a consistent and high correlation between polysomnography objective measures and the subjective quantitative measurement of sleepiness. High validity with EEG and behavioural variables was also found.

1.2 Statistical Processing:

Data was analysed using SPSS 24. Given the rather small sample size, significance testing was omitted and only descriptive data is reported.

1.3 Results:

1.3.1 Perception of Intensity, Pleasantness and Calming Effects

The fragrances were rated as more intense than the control odor PEA. The fragrances were rated as moderately intense. Odor A was perceived as most pleasant, odor C as least pleasant (but still in the neutral range and not unpleasant). In line with the pleasantness results, odor A was perceived as most calming and odor C as most energising. However odor A was on the neutral level, while odor C was rated as "energising".

1.3.2 Correlation Results:

There was a positive correlation for odor B and C, indicating that high tiredness is related to high ratings of "calming". The reverse was observed for the control odor PEA. Here high tiredness was related to the perception of the odor being "energizing". No substantial relation was observed between the odor ratings of "pleasantness" and the current positive mood of the participants—for the negative effect, there was a correlation with odor C—this odor was rated as more pleasant, the less negative effects were reported. Put differently: people will experience many negative effects, like the odor less.

1.4 Summary and Perspectives:

The results suggest that all fragrances are pleasant and moderately intense. Odor A was most pleasant and had the least energising effect, while odor C was least pleasant (rated as neutral) and had the most energising effects. Puzzlingly, odor C had the most energizing effects to those individuals were not tired. The results suggest that the effects of odor A vs C are more different than the effects of A vs B or B vs C. These preliminary results are limited by sample size.

Example 2 fMRI Study of Fragrances 2.1 Design:

23 normosmic participants (11 women) aged 20-31 years (M=23.2, SD=2.6 years) were tested. All of the participants exhibited normal olfactory function in the domains of threshold, discrimination and identification as ascertained with the Sniffing Sticks test. The functional magnetic resonance imaging (fMRI) measurement was performed with a 3 Tesla scanner. Three fragrances were presented directly to both nostrils and not diluted, as they were not diluted in the pre-test either.

In total six runs of odor presentation, each with 9 on- and 8 off-blocks, well performed in a fully balanced odor across all participants. The 2 odors presented were "Sample Active Mint Herb" (B) and "Sample Active Mint Eucalyptus" (C) as well as the control odor (PEA). Each of the odors was presented in 2 runs, in order to increase statistical power. After each run, participants were asked to rate the intensity and the pleasantness of the odor on a scale from 1 to 5 (not intense at all to very intense and not pleasant to very pleasant respectively).

The odors were applied using a computer-controlled olfactometer. Stimuli were embedded in a constant flow of odorless air (total flow 21/min). The stimuli were directed through a small tube from the olfactory to the participants' noses. 150 volumes per run were acquired by means of a 38 axial-slice matrix. Following the fMRI sessions, aT1-weighted image was acquired in sagittal direction by using a T1-MPR sequence. This scan was run to allow individualised brain normalisation in the later statistical analysis.

Additional behavioural data was acquired: participants filled in the Karolinska sleepiness scale (KSS), the PANAS and they reported how much they had slept the previous night before the fMRI measurement.

2.2 Statistical Processing:

Intensity ratings were analysed using SPSS 24. The main effect of odor quality and repetition as well as the interaction effect were modulated in a repeated measurements ANOVA. Neural data analysis was performed with the SPM 12 software implemented in Matlab are 2015b, following special pre-processing with the same software. SPM matrices reflecting the ON-OFF differences were calculated for each session, based on the general linear modelling approach. As the odors proved not to be perceived as semi-intense in the scanner, all activations were corrected for the individual intensity rating. Analysis was based on T-test with the global height threshold $P<0.001$ for the overall olfactory activation.

In addition, a gender based analysis was performed and therefore the statistical threshold was lowered to the exploratory level of $p<0.01$.

Further analysis of whether high tiredness affects the BOLD signal, the individual KSS results were included as regressor in the model. This analysis was based on a global height threshold of $p<0.001$. All activation coordinates are presented in MNI space.

2.3 Results:

2.3.1 Behavioural Data:

Participants slept 2 to 9.5 hours (M=7.2, SD 1.6 hours) before the study. The KSS showed that participants were generally rather active than sleepy (M=3.96, SD=1.71). The PANAS showed a mean score of 29.9 (SD=4.56) on the positive affect scale (Cronbach's=0.73) and a mean score of 11.8 (SD=1.81) on the negative affect scale (Cronbach=0.68).

For pleasantness ratings, there was a significant effect of repetition with the second presentation of the odor being observed as less pleasant than the first. Furthermore there was a significant effect of odors with the control being perceived as more pleasant than odor C, which was perceived as more pleasant than odor B. While odor B was perceived as "neutral", odor C was perceived rather pleasant than neutral and the control was perceived as pleasant.

For intensity ratings, there was no significant effect of repetition but a significant effect of odors with the control being perceived as less intense than odor B and C. For both intensity and pleasantness the difference between sexes of the ratings for all odors did not reach statistical significance. The results are shown in FIG. 1.

Figure 2:
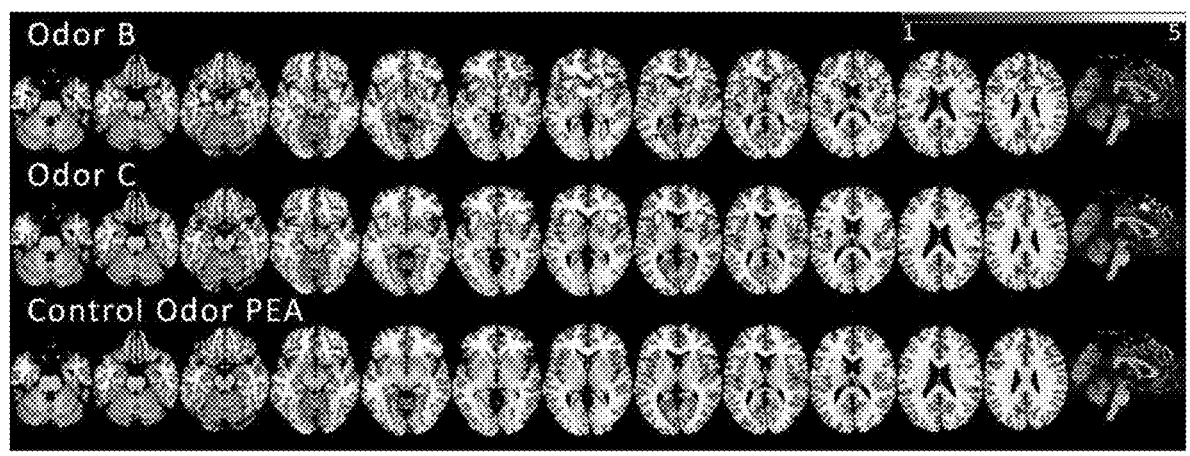
FIG. 2 Comparison of the neural activation seen following exposure to odors B, C and control. The activations vs. baseline was adjusted for intensity effects and presented on a standardized template with a high threshold of $p<0.001$, uncorrected. The scale represents the T-value.

2.3.2 Neural Results 2.3.2.1 Overall Activation:

The presentation of the fragrances was related to a clear activation of olfactory relevant areas, such as the orbitofrontal cortex, amygdala and insula (see FIG. 2).

Figure 3:
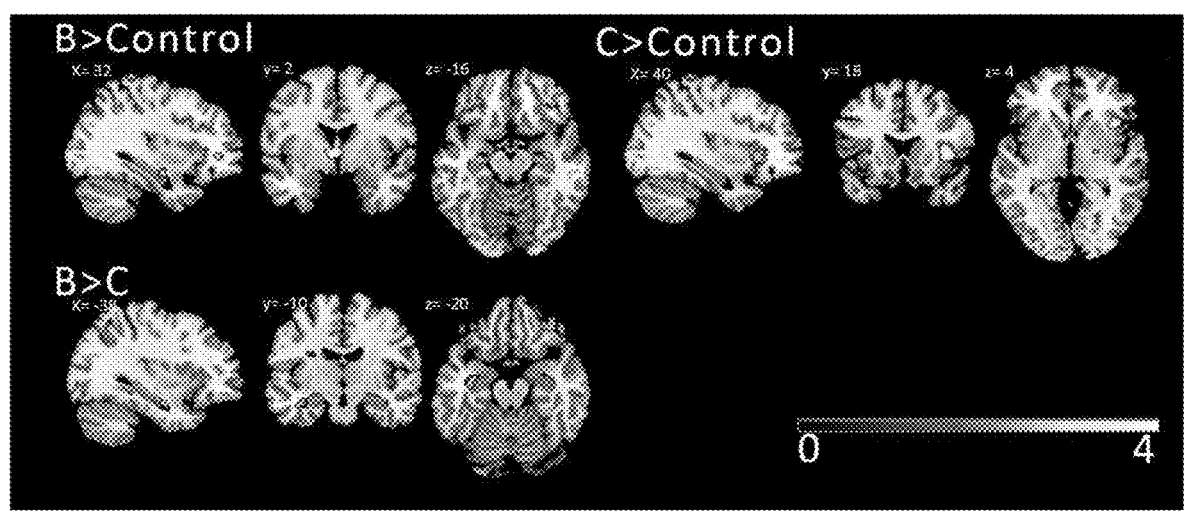
FIG. 3 Neural activation differences observed between the three presented odors: B, C and control. Odor B was related to higher BOLD signal chance in the amygdala and the hippocampus as compared to the control and as compared to the odor C (cave: for the comparison to the control, the activation difference is on the right side, for the comparison to odor C it is on the left side). Odor C produced enhanced activation in relation to the control odor in the IFG, extending to the right anterior insula. As there was no major activation in C>B, this contrast is not displayed. The threshold level is set to $p<0.001$ (uncorrected). The scale represents the T-values.

2.3.2.2 Odor B:

Odor B vs control: the odor B was related to higher BOLD signal changes in the caudate, putamen, superior or orbital gyrus, amygdala and hippocampus. Odor B vs odor C: the enhanced activation in the amygdala was also observed in relation to odor C. In addition, odor B produced enhanced activation in the anterior cingulate gyrus as well as in the inferior temporal gyrus and in the fusiform gyrus. (see FIG. 3)

2.3.2.3 Odor C:

Odor C vs control: as compared to the control odor, odor C produce enhanced activation in the orbitofrontal gyrus, extending to the right insula and in the interior parietal lobule. Odor C vs odor B: there was only a very slight enhanced activation in odor C as compared to odor B, located in the inferior parietal lobule. (see FIG. 3)

2.3.2.4 Sex Differences:

For men and women, odor B and odor C resulted in an activation of olfactory related areas, especially the insula was robustly activated. The gender-specific comparison revealed no significant difference at the conventional $p<0.001$ height threshold. Exploratory comparison with a threshold of $p<0.01$ reveal and enhance caudate activation in women in odor B and odor C as compared to men.

Figure 4:
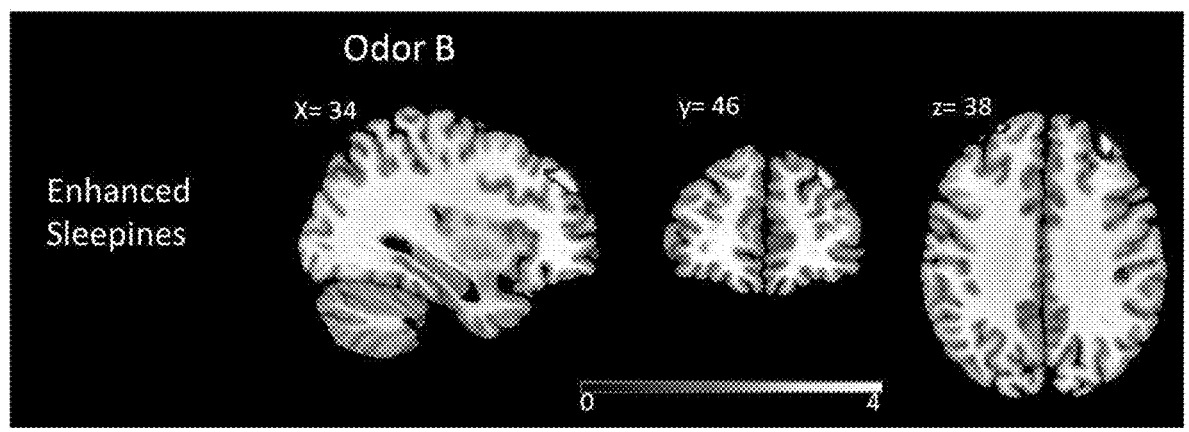
FIG. 4 Neural activation of odor B in relation to the participants' tiredness. The more tired the participants were, the more DLP FC activation resulted after inhaling odor B. The threshold level is set to $p<0.001$ (uncorrected). The scale represents the T-values.

2.3.2.5 KSS Covariate Analysis:

Using the individual scores of the KSS as a covariate, the following results emerge: for odor B, higher KSS scores, which indicates subject's sleepiness, where related to stronger activation of the left and right middle frontal gyrus, which contains the dorsal lateral prefrontal gyrus (DL PFC). This cluster was not activated in people with low KSS scores, hence in people who were awake. The DL PFC is implicated in executive functions such as decision-making and working memory. (see FIG. 4)

Figure 5:
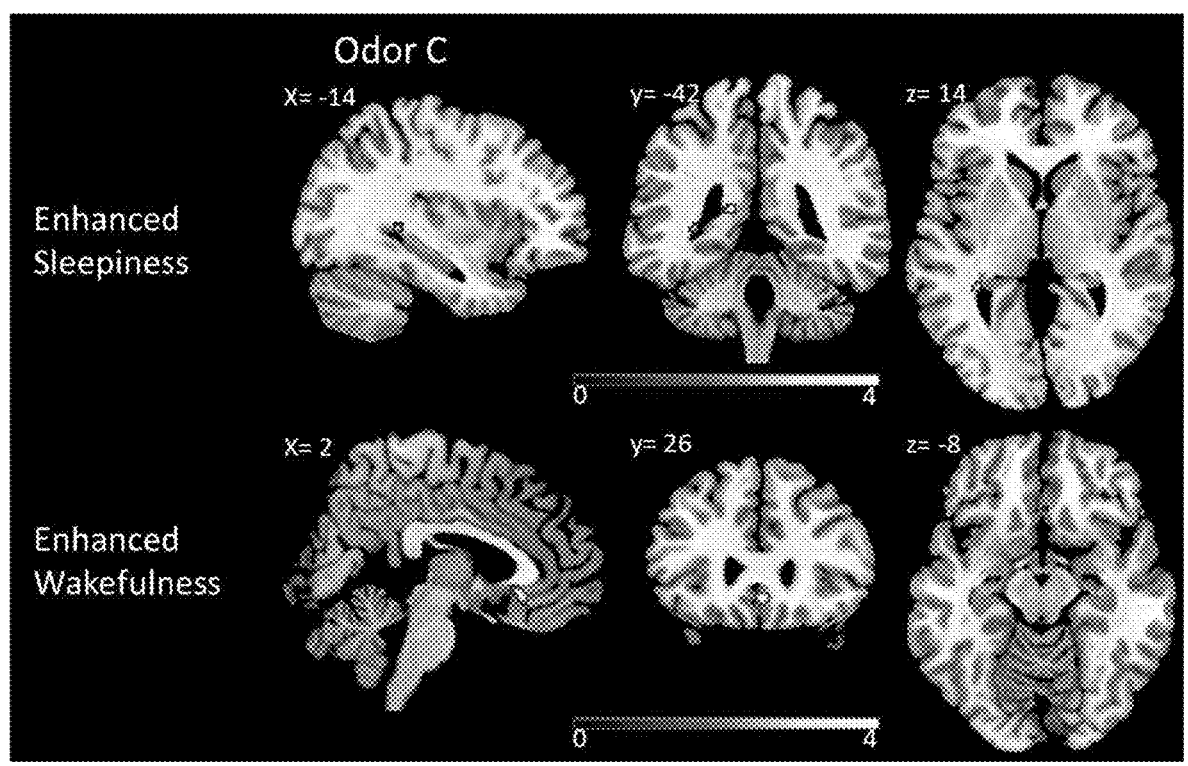
FIG. 5 Neural activation of odor C controlled for subjects' sleepiness or wakefulness respectively. The threshold level is set to $p<0.001$ (uncorrected). The scale represents the T-values It is to be expressly understood that the description and drawings are only for the purpose of illustrating certain embodiments of the present disclosure and are an aid for understanding. They are not intended to be a definition of the limits of the disclosure and/or of the technology.

For odor C, higher KSS course were related to an activation in the left hippocampus. Low KSS scores, on the other hand, where related to more activation in the middle orbital gyrus, which is related to executive functions. This area was deactivated in people with high KSS scores. Hence a high sleepiness was related to an activation of the hippocampus and a deactivation of the middle orbital gyrus. (see FIG. 5)

2.4 Summary and Perspectives:

Both fragrances B and C resulted in a much higher neural activation than the control odor. This was still present after controlling for the subjective intensity perception. The likely reason is the more wide spread receptor binding, produced by mixtures of odors than by single molecules. Odor B had the most pronounced activation as compared to both, the control and odor C. In comparison to both odors, odor B activated the amygdala stronger. In comparison to the control odor, odor B led to stronger activation of reward areas (putamen, caudate). In comparison to odor C, odor B led to higher activation of the anterior cingulate gyrus, an area related to satience processing. Odor B was related to a higher activation of executive brain areas (DL PFC) in those participants who were most sleepy. This was not observed for odor C. For this odor, high sleepiness was related to higher activation of the hyper campus and to and deactivation of the middle orbital gyrus. There were no major sex differences for neural effects of the odors.

The present technology is not to be limited in scope by the specific embodiments described herein. Indeed, various modifications of the present technology in addition to those described herein will become apparent to those skilled in the art from the foregoing description and accompanying figures. Such modifications are intended to fall within the scope of the appended claims. Moreover, all aspects and embodiments of the present technology described herein are considered to be broadly applicable and combinable with any and all other consistent embodiments, including those taken from other aspects of the present technology (including in isolation) as appropriate.

Various publications and patent applications are cited herein, the disclosures of which are incorporated by reference in their entireties.

The invention claimed is:

1. A fragrance composition consisting of comprising:
   (a) *Lavandula hybrida* Oil;
   (b) *Rosmarinus offinalis* Leaf Oil; and
   (c) *Mentha piperita* Oil.

2. The fragrance composition according to claim 1, wherein the ratio of (a) to (b) is from 1.5:1 to 2.5:1 and/or the ratio of (b) to (c) is from 1:1 to 1.5:1.

3. The fragrance composition according to claim 2, wherein the ratio of (a) to (b) is about 2:1 and/or wherein the ratio of (b) to (c) is about 1.25:1.

4. The fragrance composition according to claim 1, consisting of:
   (a) about 54% *Lavandula hybrida* Oil;
   (b) about 26% *Rosmarinus offinalus* Leaf Oil; and
   (c) about 20% *Mentha piperita* Oil.

5. A method of reducing fatigue in a subject, the method comprising administering to the subject a fragrance composition according to claim 1.

6. A method of improving executive brain function in a subject, the method comprising administering to the subject a fragrance composition according to claim 1.

7. A cosmetic product comprising the fragrance composition according to claim 1.

8. The cosmetic product according to claim 7, wherein the product is a cream, a lotion, a spray composition, an infused wipe, a face mask, drops, or a body soil.

9. The cosmetic product according to claim 7, wherein the product further comprises vitamin C.

10. The cosmetic product according to claim 7, wherein the product is a cream and comprises the fragrance composition in an amount of from 0.1 to 5 wt %.

11. A candle comprising the fragrance composition according to claim 1.

12. A spray device comprising a spray nozzle in fluid communication with a reservoir, the reservoir containing the fragrance of claim 1 and a volatile solvent.

13. A fragrance composition consisting of:
   (a) about 50-58% *Lavandula hybrida* Oil;
   (b) about 22-30% *Rosmarinus offinalis* Leaf Oil; and
   (c) about 16-24% *Mentha piperita* Oil.

14. A cosmetic product comprising the fragrance composition according to claim 13.

15. The cosmetic product according to claim 14, wherein the product is a cream, a lotion, a spray composition, an infused wipe, a face mask, drops, or a body oil.

16. The cosmetic product according to claim 14, wherein the product further comprises vitamin C.

17. The cosmetic product according to claim 14, wherein the product is a cream and comprises the fragrance composition in an amount of from 0.1 to 5 wt %.

* * * * *